United States Patent [19]

Banuchi

[11] Patent Number: 5,800,446

[45] Date of Patent: Sep. 1, 1998

[54] ARTICLE AND METHOD FOR DERMABRADING

[76] Inventor: Isabel M. Banuchi, Avenida Domanech 302, Hato Bay, Puerto Rico, 00918

[21] Appl. No.: 807,362

[22] Filed: Feb. 27, 1997

[51] Int. Cl.[6] .............................. A61B 17/50; A41D 19/00
[52] U.S. Cl. ................................... 606/131; 2/161.8
[58] Field of Search ........................ 606/131; 2/159, 2/160, 161.1–161.8

[56] References Cited

U.S. PATENT DOCUMENTS

| | | | |
|---|---|---|---|
| 132,468 | 10/1872 | Jacobsohn | 606/131 |
| 2,465,136 | 3/1949 | Troccoli | 2/161.6 |
| 5,642,527 | 7/1997 | Savage | 2/161.6 |

*Primary Examiner*—Glenn K. Dawson
*Attorney, Agent, or Firm*—Parkhurst & Wendel, LLP

[57] ABSTRACT

A method of removing an epidermal portion of the skin of a patient by dermabrading, including the steps of providing a disposable dermabrasion tool having an elongated body having a stick handle and a working end. The working end includes a rounded abrasive tip that is enlarged with respect to the stick handle. The stick handle of the dermabrasion tool is grasped and the working end is pressed against the skin of a patient. The working is rubbed end against the skin to remove the epidermal portion. The present invention also provides a disposable glove embodiment having abrasive regions for dermabrading.

5 Claims, 3 Drawing Sheets

ARTICLE AND METHOD FOR DERMABRADING

BACKGROUND OF THE INVENTION

The present invention relates to a method and article for smoothing irregularities and camouflaging scarring of the skin of a patient, by dermabrasion. Dermabrasion generally consists of removing the epidermis and superficial layers of the dermis. Dermabrasion can be used as a therapeutic process for several conditions. In particular, indications for dermabrasion include acne scarring, active acne, nasal rhinophyma, traumatic or surgical scarring, tattoos, lentigenes, facial rhytids, and keratoses.

DISCUSSION OF THE PRIOR ART

Presently, dermabrasion is carried out by utilizing powered air-driven units. Such units include a tip that rotates at high speed, for example, 600 to 35,000 RPM. The tip receives a sanding bit, which is rotated by the tip while it is pressed against the dermis of a patient. In this way, the epidermal layer of skin may be removed, which effects removal of superficial scars of the skin and improvement in appearance of intermediate depth scars. Following dermabrasion, a new layer of epidermis forms at a depth or level lower than that of the original epidermis. Dermabrasion may be carried out several times to treat deep scarring of the skin.

Despite the efficacy of utilizing powerful air-driven units according to the prior art, such units have several drawbacks. For example, such units are costly and relatively complex. Further, the inventor has recognized a need in the art for a method of effecting fine touch-up of portions of the skin by dermabrasion, following use of automated dermabrasion units.

SUMMARY OF THE INVENTION

The present invention has been developed to overcome the disadvantages of the prior art discussed above. In particular, the present invention has been developed to provide a method which is simple, easy and economical to carry out, and which can be used for fine touch-up of the skin following a major dermabrasion procedure. In addition, the present invention has been developed to provide a novel article that can be utilized to provide fine touch-up of the skin, which is easy to use, economical and disposable.

To these ends, a first aspect of the present invention provides a method for removing an epidermal portion of the skin of a patient by dermabrading, including (1) providing a disposable dermabrasion tool having an elongated body including a stick handle and a working end, the working end including a rounded abrasive tip that is enlarged with respect to the stick handle, (2) grasping the stick handle of the dermabrasion tool and pressing the working end against the skin of the patient, and (3) rubbing the working end against the skin to remove the epidermis.

The procedure may further include removing superficial layers of the skin below the epidermis. Additionally, the skin may be frozen before dermabrasion, for example, by application of freon or ice. Freezing generally stiffens the skin which aids in efficient and accurate removal of desired portions of the epidermis.

Preferably, the dermabrasion tool, including the stick handle and the working end, is formed of a unitary body, for example, injection molded plastic material or wood. The material should be of sufficient rigidity so as to resist deformation due to contact pressure of the tool against the skin. Furthermore, the working end preferably has abrasive grains adhered to an outer surface thereof. A plurality dermabrasion tools may be provided in kit form, including tools having various grits, like differing grits of sandpaper.

A second aspect of the present invention provides an article for removing an epidermal portion of the skin of a patient by dermabrading, including a disposable glove including a main body having an opening and anterior (palmer) and posterior regions for respectively covering the anterior (palmer) and posterior portions of the hand of the wearer, and the plurality of finger extensions extending from the main body and wrapping around anterior and posterior surfaces of the fingers, and at least one abrasive region provided on a finger extension of the glove, along an anterior outer surface thereof.

The abrasive region may be provided by adhering abrasive grains to appropriate anterior surface portions of the glove, or by adhering adhesive sandpaper to appropriate portions of the glove. Additionally, the glove may be made from latex material, as is known in the art.

In particular embodiments, the abrasive regions extend over a palmer portion of the glove including that portion of the glove that covers the heel of the palm of the wearer. This region may be utilized to carry out dermabrasion with respect to relatively large areas of the skin in contrast with more precise dermabrasion that may be carried out by manipulating the finger extensions of the glove. If a plurality of abrasive regions are provided along different anterior surfaces of the glove, the abrasive regions may have differing grits, so that the user may chose the particular coarseness of the abrasive material as appropriate.

The finger extensions of the glove are preferably divided into three regions, including a proximal phalange region, a medial phalange region, and a distal phalange region, and the abrasive region is provided at least along the distal phalange region of one of the finger extensions. Preferably, the abrasive region extends around so as to cover a distal tip region that covers the tip of the finger of the wearer so that dermabrasion may be carried out with exceptional accuracy.

According to a third aspect of the present invention, a method is provided for removing an epidermal portion of the skin of a patient by dermabrading, utilizing the article described above with respect to the second aspect of the present invention. Particularly, the glove is fitted on the hand of the wearer, and at least one abrasive region is rubbed against the skin to remove the epidermal portion. As with the method of the first aspect of the present invention, the method may be carried out to remove layers of the skin below the epidermis. In addition, the skin may be frozen prior to dermabrasion to aid in efficient and accurate removal of desired portions of the epidermis.

DETAILED DESCRIPTION OF THE PREFERRED EMBODIMENTS

Figure 1:
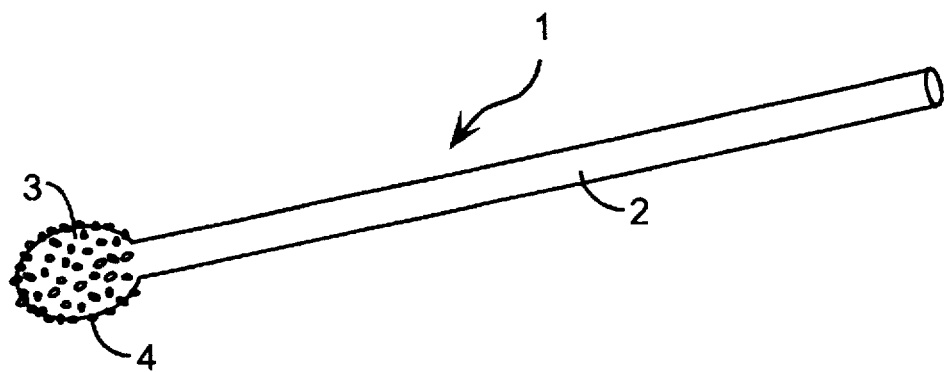
FIG. 1 is a perspective view of the dermabrasion tool used in accordance with the method of the present invention.
Figure 2:
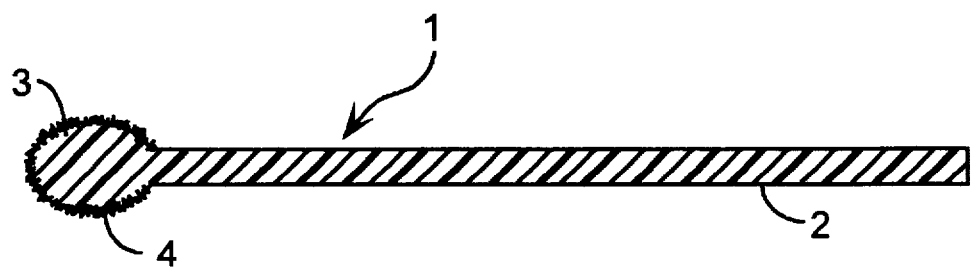
FIG. 2 is a cross-section of the dermabrasion tool illustrated in FIG. 1.

FIGS. 1 and 2 illustrate a dermabrasion tool used in accordance with a method of the present invention. Tool 1 has a generally elongated body, including stick handle 2 and working end 3. As shown, the working end 3 has a rounded outer contour, notably lacking any sharp or discrete edges or corners. In addition, the working end 3 is enlarged with respect to the diameter of the stick handle 2, increasing the working surface area thereof. Further, abrasive grains 4 are embedded in the outer surface of the working end 3. Preferably, the tool 1 is about three to seven inches long, the stick handle 2 thereof having a diameter that allows the physician to securely grasp the tool 1. Preferably, the tool 1 is formed of a 1-piece integral body, such as injection molded plastic material or wood.

According to the present method, the user grasps the tool as described above, presses the working end against the desired portion of the skin of the patient, and rubs the working end against the skin to remove desired portions of the epidermis. The procedure is highly effective and significantly reduces superficial scarring and improves the appearance of intermediate depth scars. Over the course of several months, dermabrasion may be repeated to alleviate very deep scars.

Figure 3:
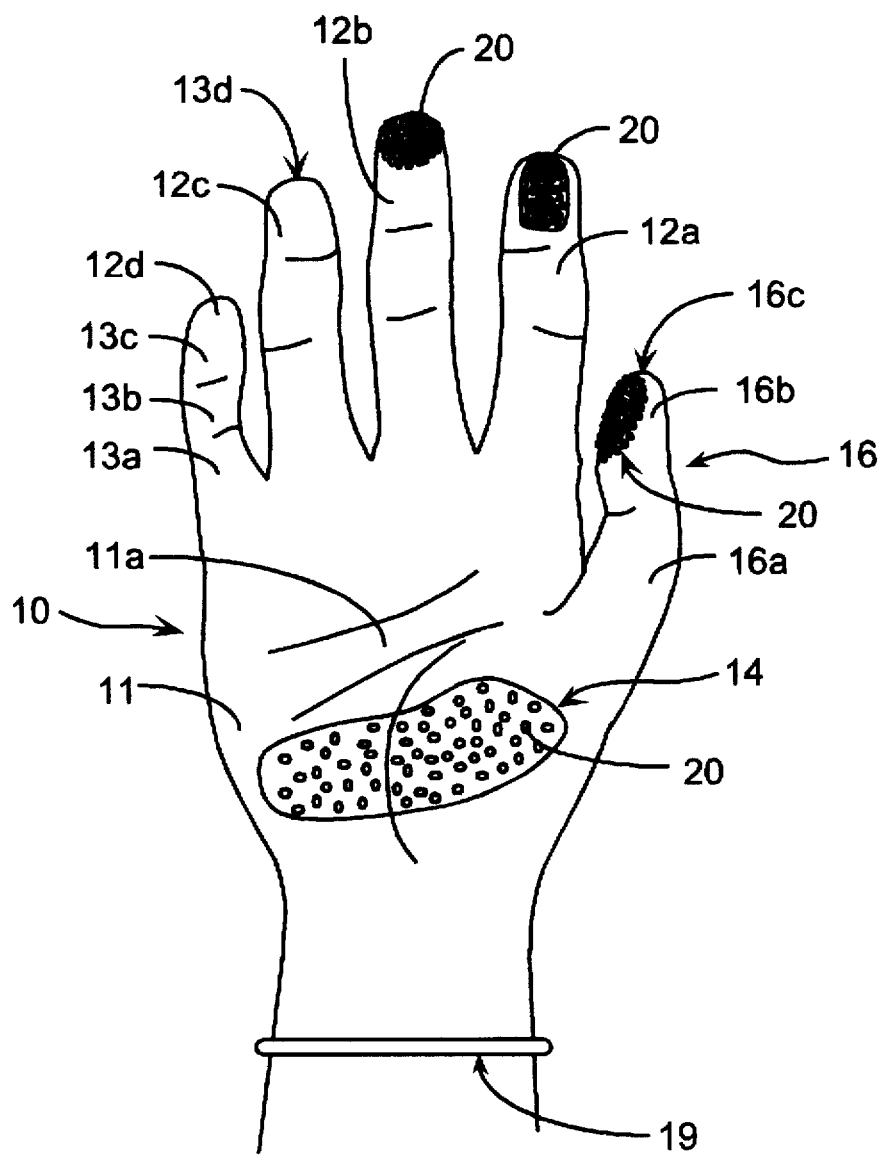
FIG. 3 is an anterior (palmer) perspective view of the dermabrasion glove fitted on the hand of a wearer.
Figure 4:
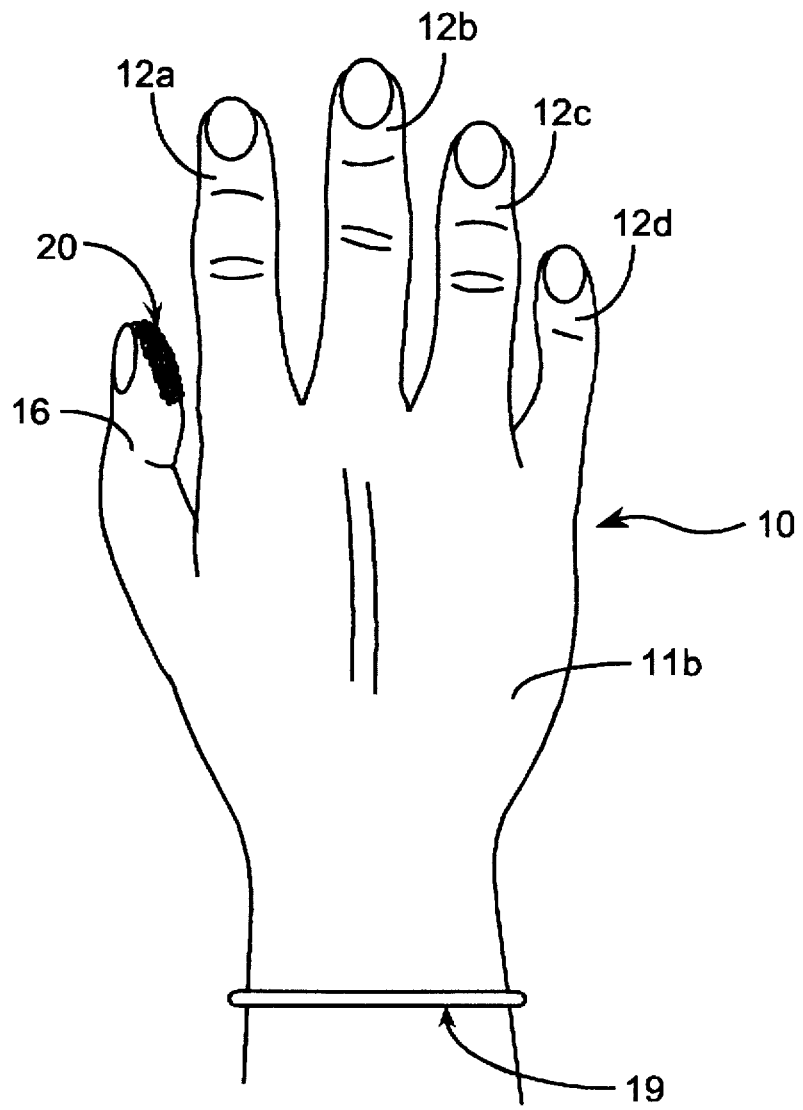
FIG. 4 is similar to FIG. 3 but shows the posterior view of the dermabrasion glove fitted on the hand of the wearer.

FIGS. 3 and 4 respectively illustrate anterior (palmer) and posterior views of the dermabrasion glove in accordance with one aspect of the present invention. The glove 10 includes a main body 11 having an opening 19 and palmer and posterior regions 11a and 11b respectively covering palmer and posterior portions of the hand of the wearer. A plurality of finger extensions, including first, second, third and forth finger extensions 12a through 12d, respectively, extend from the main body 11 and wrap around anterior and posterior surfaces of respective first through forth fingers of the wearer. As shown, each finger extension is divided into proximal phalange region 13a, medial phalange region 13b and distal phalange region 13c. In addition, the distal phalange region 13c includes distal tip region 13d that covers the respective tip of the fingers of the wearer.

The glove 10 further includes thumb extension 16 that includes proximal phalange region 16a and distal phalange region 16b for respectfully receiving proximal and distal phalanges of the thumb of the wearer.

According to a particular development of the present invention, abrasive regions 20 are provided along desired anterior regions of the glove. As shown in FIG. 3 in particular, an abrasive region 20 is provided on the distal phalange region 13c of first finger extension 12a and on distal phalange region 13c of second finger extension 12b. As shown with respect to second finger extension 12b, the abrasive region may preferably extend onto and cover the distal tip region 13d of the finger extension.

To enhance further the efficiency of removal of the epidermis, abrasive regions 20 may be provided along the palmer region of the glove, particularly, along the heel region 14 of the palmer region 11a. Further, an abrasive region may be provided on an anterior surface of the distal phalange region 16b of thumb extension 16, and extend onto distal tip region 16c of thumb extension 16.

In practice, the glove 10 is fitted onto a hand of the wearer, and abrasive regions thereof are rubbed against the skin to remove the epidermal portion of the patient.

While the particular embodiment shown in FIGS. 3 and 4 has been illustrated with particularity modifications may be made thereto without departing from the spirit and scope of the invention as defined in the appended claims. For example, each finger extension may receive an abrasive region, and a larger area of the palmer region may be provided with abrasive material. Additionally, not all fingers need be covered by finger extensions. The particular embodiment of the glove may be modified to suit the needs of the wearer, that is, the physician.

I claim:

1. A method of removing an epidermal portion of the skin of a patient by dermabrading, comprising the steps of:

providing a disposable dermabrasion glove including (i) a main body having an opening and palmar and posterior regions for respectively covering palmar and posterior portions of the hand of the wearer, (ii) a plurality of finger extensions extending from the main body and wrapping around anterior and posterior surfaces of the fingers, and (iii) at least one abrasive region provided on a finger extension of the glove, along an anterior outer surface thereof;

fitting the glove on a hand of the wearer;

rubbing the at least one abrasive region against the skin to remove the epidermal portion.

2. The method of claim 1, further comprising removing layers of the skin below the epidermis.

3. The method of claim 1, further comprising freezing the skin before pressing the abrasive region against the skin.

4. The method of claim 3, wherein the skin is frozen by applying freon.

5. The method of claim 3, wherein said skin is frozen by applying ice.

* * * * *